United States Patent [19]

Stoeffler

[11] Patent Number: 5,174,453
[45] Date of Patent: Dec. 29, 1992

[54] TRAY SYSTEM FOR SURGICAL INSTRUMENTS

[76] Inventor: Jill Stoeffler, 9725 E. Harvard Ave., Suite BB454, Denver, Colo. 80231

[21] Appl. No.: 888,810

[22] Filed: May 27, 1992

[51] Int. Cl.[5] .................. B65D 85/62; B65D 1/34
[52] U.S. Cl. .................. 206/570; 206/370; 206/439; 206/561
[58] Field of Search .......... 206/370, 369, 363, 372, 206/439, 438, 561, 564, 557, 459, 570, 486; 422/300, 310, 297

[56] References Cited

U.S. PATENT DOCUMENTS

| | | | |
|---|---|---|---|
| 4,053,280 | 10/1977 | Salisbury | 206/363 |
| 4,293,074 | 10/1981 | Dunsky | 206/369 X |
| 4,353,694 | 10/1982 | Pelerin | 206/370 X |
| 4,643,303 | 2/1987 | Arp et al. | 206/370 |
| 4,716,025 | 12/1987 | Nichols | 206/363 X |
| 4,798,292 | 1/1989 | Hauze | 206/363 X |
| 4,959,199 | 9/1990 | Brewer | 206/439 X |
| 4,978,510 | 12/1990 | Smith | 206/439 X |
| 5,046,624 | 9/1991 | Murphy et al. | 206/370 X |

Primary Examiner—Paul T. Sewell
Assistant Examiner—Jacob K. Ackun, Jr.
Attorney, Agent, or Firm—William E. Hein

[57] ABSTRACT

A surgical tray system includes an enclosure base, a U-shaped instrument rack removably positioned within the enclosure base and capable of suspending a complete set of surgical operating instruments by their shafts, a flat operative assembly tray that may be locked into position on top of the enclosure base, above the U-shaped instrument rack, for retaining additional surgical instruments in positions that are identified by silk-screened outlines of those additional instruments, and a cover that may be locked into position on top of the operative assembly tray, thereby covering the enclosure base, the U-shaped instrument rack positioned within the enclosure base, and the operative assembly tray. One or more additional trays, such as a diagnostic assembly tray, for retaining additional instruments required in connection with a particular surgical procedure, may be stacked above or below the operative assembly tray or they may be included within a separate tray having its own enclosure base and cover.

11 Claims, 3 Drawing Sheets

TRAY SYSTEM FOR SURGICAL INSTRUMENTS

BACKGROUND AND SUMMARY OF THE INVENTION

This invention relates generally to surgical instrument trays and more specifically to a tray system that is designed to house all of the operating instruments required for advanced endoscopic procedures, whether general, gynecologic or thoracic, in a logically organized fashion such that missing instruments may be readily identified prior to commencement of a procedure.

In all endoscopic surgical procedures, whether abdominal or thoracic, a group of operating instruments is required to perform an anticipated surgical procedure following a diagnostic procedure in which the surgeon employs an additional set of access instruments to gain access to the operative site. Protection and organization of such operating instruments is essential to the successful outcome of the surgical procedure. Damage to these sensitive instruments has a significant economic impact on a healthcare facility, both in terms of repair and replacement costs, as well as lost revenues due to case cancellations and surgeon discontent.

A number of so-called surgical instrument trays are known in the prior art. However, most of these prior art trays amount to nothing more than storage cases that are inconvenient, if not impossible, to use in the working environment of an operating room. Several known surgical instrument storage cases are simply covered shallow containers in which surgical instruments are randomly placed. Some of these shallow containers include foam rubber bottom linings in an attempt to protect the instruments stored therein. Another known surgical instrument storage case is capable of holding only six operative instruments, a number considered inadequate to complete a typical endoscopic surgical procedure. However, these six instruments are retained in stacked relationship with each other, thereby making acquisition of a particular instrument difficult, at best. Yet another known surgical instrument storage case provides only ten spaces for instruments having shaft diameters of five millimeters. Since various commercially available surgical operating instruments have shaft diameters of five, ten or twelve millimeters, any surgical tray system of value in an operating room environment must be able to accommodate instruments of all three of these sizes.

Silicon rubber inserts are available for positioning as desired on the bottom surface of certain types of these conventional shallow instrument trays to hold several instruments in fixed positions. This storage arrangement, like others in the prior art, results in haphazard positioning of the instruments, with the handles of some of the instruments at one end of the tray and those of others of the instruments at the opposite end of the tray, again making acquisition of a particular instrument difficult and subjecting the instruments to possible damage as the result of contact by adjacent instruments.

It is therefore the principal object of the present invention to provide a tray system for retaining a set of surgical instruments for convenient use in an operating room environment, organized according to their logical order of use by surgical personnel and in a way that protects them from damage, that permits easy identification of any missing instruments, and that also permits them to be easily sterilized without removing or otherwise disturbing their positions within the tray system.

This and other objects are accomplished in accordance with the illustrated preferred embodiment of the present invention by providing an enclosure base, a U-shaped instrument rack positioned within the enclosure base capable of suspending a complete set of operating surgical instruments by their shafts such that the handles of the instruments freely depend from their shafts, a flat operative assembly tray that may be locked into position on top of the enclosure base, above the U-shaped instrument rack, for retaining additional surgical instruments in positions that are identified by silk-screened outlines of those additional instruments, and a cover that may be locked into position on top of the operative assembly tray, thereby covering both the U-shaped instrument rack within the enclosure base and the flat operative assembly tray.

DETAILED DESCRIPTION OF THE PREFERRED EMBODIMENT

Figure 1:
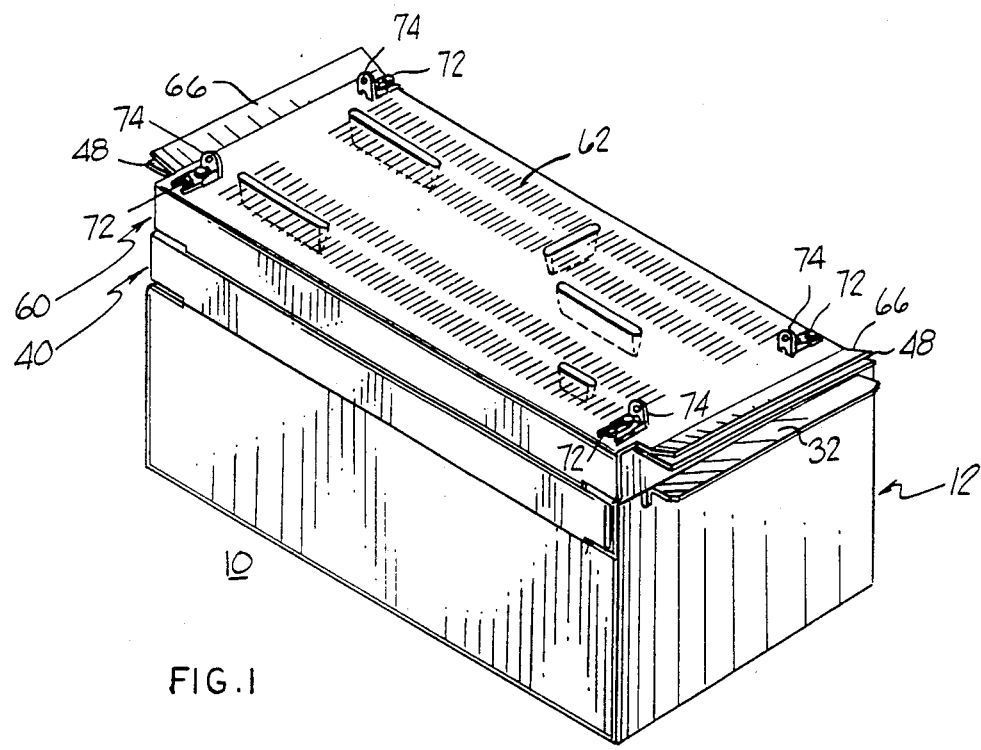
FIG. 1 is a pictorial diagram of the assembled surgical tray system for retaining surgical instruments constructed in accordance with the present invention.
Figure 2:
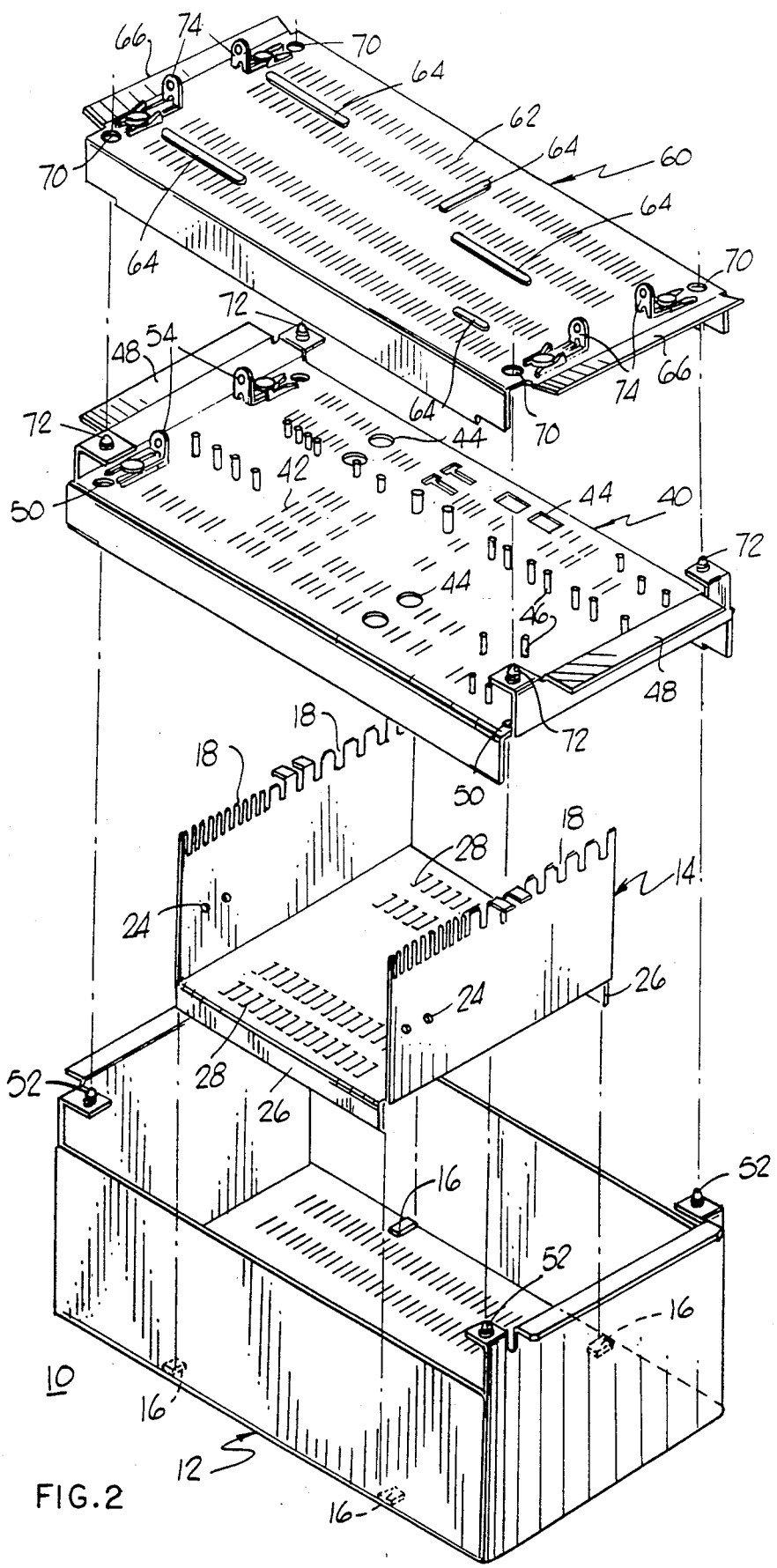
FIG. 2 is an assembly diagram of the surgical tray system of FIG. 1.
Figure 3:
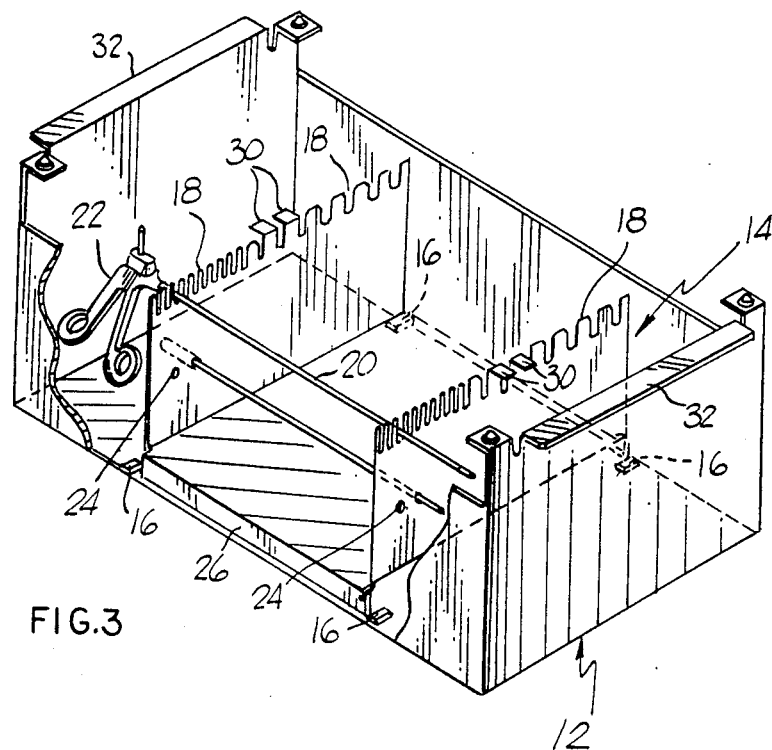
FIG. 3 is a pictorial diagram of enclosure base and U-shaped instrument rack components of the tray system of FIGS. 1 and 2.

Referring now to FIG. 1, there is shown an overall pictorial diagram of the assembled components of a surgical tray system 10 for retaining a complete set of surgical operating instruments. Referring also to the assembly diagram of FIG. 2, tray system 10 includes a rectangular enclosure base 12 and a U-shaped instrument rack 14. U-shaped instrument rack 14 is positioned within enclosure base 12, as illustrated in FIG. 3, to rest on the floor thereof. Four raised retention members 16 are provided on the floor of enclosure base 12 to prevent slippage of U-shaped instrument rack 14. Each vertical side member of U-shaped instrument rack 14 includes a corresponding plurality of slots 18 for receiving and supporting the shafts of a set of surgical operating instruments required to perform an endoscopic surgical procedure, exemplary of which is the surgical instrument illustrated in FIG. 3 having a shaft 20 and a freely depending handle 22 at one end thereof. Groups of the slots 18 are formed to have different widths to accommodate surgical instruments having shafts of various standard diameters. For example, one group of the slots 18 are formed to be ten millimeters in width, while another group of the slots 18 are formed to be six millimeters in width to accommodate the shafts of the correspondingly-sized surgical instruments being retained therein. By supporting the surgical instruments by their shafts, the handles of those instruments are permitted to hang in the vertical position illustrated, thereby facilitating removal of a desired instrument and insuring that the instruments do not interfere with each other. This arrangement also allows the surgical team to quickly recognize the absence of a particular instrument and helps prevent damage to an instrument that is typically caused by contact with an adjacent instrument. One or more corresponding pairs of holes 24 in the side walls of U-shaped instrument rack 14 are provided to retain suction tubes and their obturators, for example, and/or other instruments deemed necessary by the surgical team. U-shaped instrument rack 14 is formed to include feet members 26 on two sides thereof to slightly elevate it off the floor of enclosure base 12. A plurality of vent slots 28 are also provided on the bottom surface of U-shaped instrument rack 14 to promote movement of air during sterilization processes. U-shaped instrument rack 14 includes a pair of outwardly extending flanges 30 on each of the side walls thereof to serve as handles. Similarly, enclosure base 12 includes flanges 32 serving the same purpose.

Figure 6:
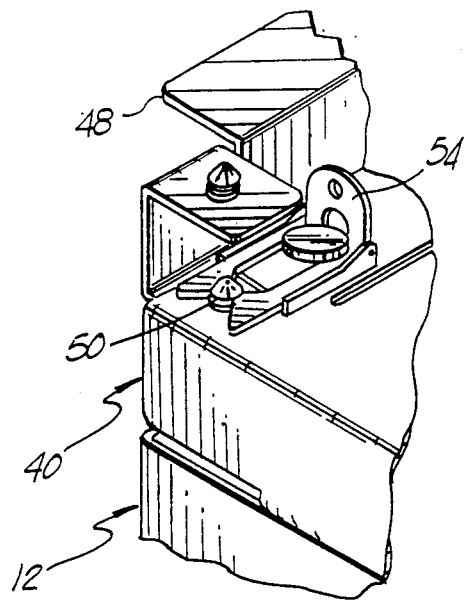
FIG. 6 is a partial pictorial diagram illustrating the details of one of the operative assembly tray fasteners employed in the surgical tray system of FIGS. 1 and 2.
Figure 4:
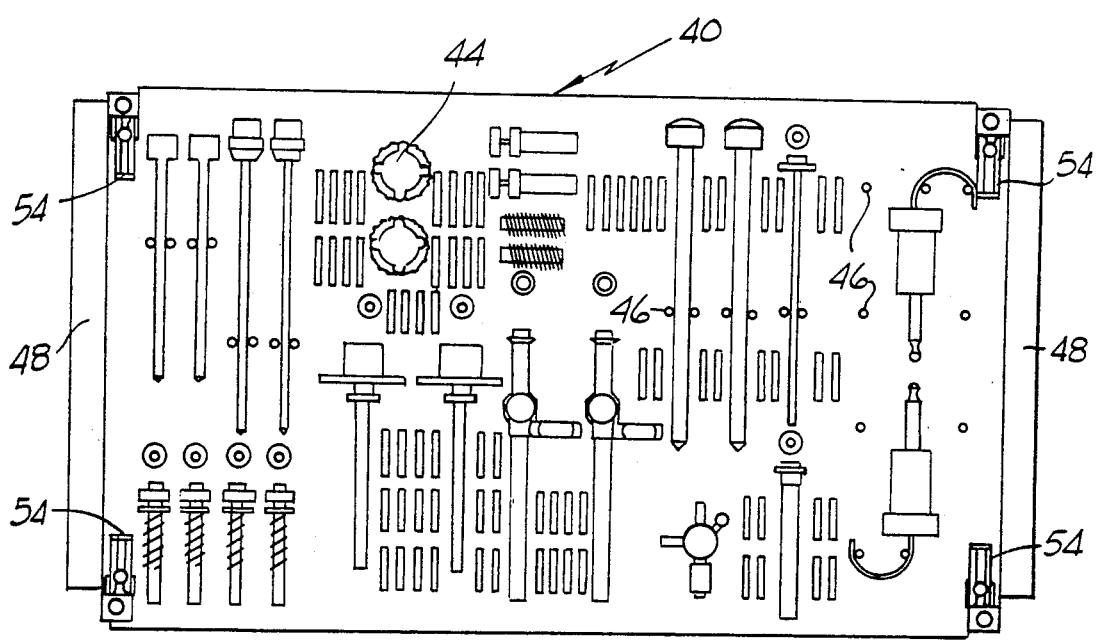
FIG. 4 is a plan view of an operative assembly tray employed in the surgical tray system of FIGS. 1 and 2.

Referring again to FIG. 2, tray system 10 further includes a generally flat rectangular operative assembly tray 40 designed for retaining additional instruments, such as trocars and sheaths/access ports that may be required for advanced general, gynecological, and thoracic endoscopic surgical procedures. As shown in the detailed plan view of FIG. 4, operative assembly tray 40 includes a plurality of vent slots 42, as well as pluralities of apertures 44 and upwardly extending guide members 46 for retaining the disassembled parts of the required additional instruments. A silk-screened or otherwise marked silhouette of each instrument part is provided on the top surface of operative assembly tray 40 to simplify placement of all of the instrument parts and to provide quick and easy recognition of any missing parts in the early phases of case preparation by both the instrument room personnel and the surgical team. The disassembled instrument parts retained on operative assembly tray 40 are preferably arranged in the order of their use during a particular procedure. Operative assembly tray 40, like enclosure base 12, includes a pair of outwardly extending flanges 48 on the sides thereof to serve as handles. Operative assembly tray 40 also includes four holes 50 positioned adjacent the corners thereof for receiving correspondingly positioned, upwardly projecting positioning studs 52 fixedly provided at each of the top corners of enclosure base 12. Conventional sliding spring clips 54 act to engage positioning studs 52 to thereby lock operative assembly tray 40 in place on top of enclosure base 12. The details of the sliding locking and unlocking action of one of spring clips 54 over a corresponding one of the positioning studs 52 are illustrated in FIG. 6.

Figure 5:
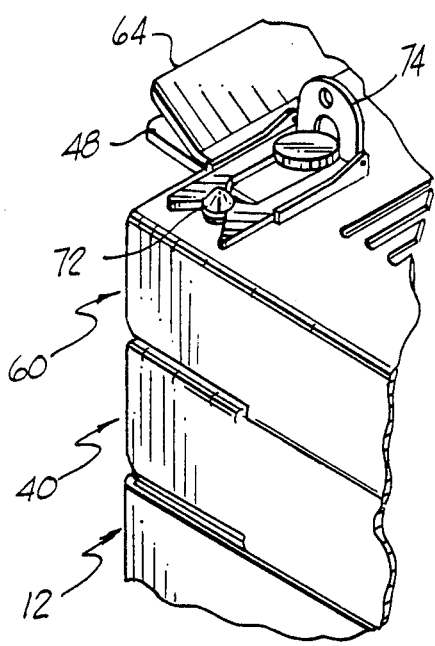
FIG. 5 is a partial pictorial diagram illustrating the details of one of the cover fasteners employed in the surgical tray system of FIGS. 1 and 2.

Referring again to FIGS. 1 and 2, a generally flat rectangular lid or cover 60 is provided to cover operative assembly tray 40 to thereby complete the assembly of tray system 10. Cover 60, like the other components of tray system 10 described above, includes a plurality of vent slots 62. Several downwardly projecting strips 64, fabricated of high grade medical silicone, are fixedly positioned on cover 60 to exert gentle pressure on each of the instrument parts retained on operative assembly tray 40 when cover 60 is locked into position over operative assembly tray 40. Cover 60, like operative assembly tray 40, includes a pair of outwardly extending flanges 66 to serve as handles. Flanges 66 extend slightly upwardly to permit them to be grasped separately from flanges 48 of operative assembly tray 40. Like operative assembly tray 40, cover 60 also includes four holes 70 positioned adjacent the corners thereof for receiving corresponding positioned, upwardly projecting positioning studs 72 fixedly provided at each of the top corners of operative assembly tray 40. Sliding spring clips 74 act in the same way as sliding spring clips 54 on operative assembly tray 40 to engage respective ones of the positioning studs 72 to thereby lock cover 60 in place on top of operative assembly tray 40. The details of the sliding locking and unlocking action of one of spring clips 54 over a corresponding one of positioning studs 72 are illustrated in FIG. 5.

If desired, additional trays similar in construction to operative assembly tray 40 may be provided to hold additional surgical instruments required to perform a particular endoscopic surgical procedure. For example, a diagnostic tray may be provided to retain all of the diagnostic instruments required in connection with an anticipated surgical procedure. Such a diagnostic tray may be stacked between operative assembly tray 40 and cover 60 or it may be separately combined with an enclosure basis similar to enclosure base 12 and a cover like cover 60.

The components of the tray system 10 described in detail above may be fabricated of any of a number of commercially available materials, but anodized aluminum has been found to be a preferable material. In use, the entire assembled tray system 10, after being loaded with the complete set of surgical instruments required to perform a particular surgical procedure, may be placed in a sterilization chamber, commonly referred to as an autoclave. Therefore, the material chose for fabrication of tray system 10 should be one that can be subjected to the sterilization procedures in general use in hospitals. Following the sterilization process, the entire tray system 10 in assembled form may be placed on a conventional mayo tray or back table in the operating room, ready for removal of the various surgical instruments retained therein in the order in which they are required by the surgical team.

I claim:
1. A surgical tray system for retaining a plurality of surgical instruments, the surgical tray system comprising:
   an enclosure base, said enclosure base having a horizontal floor member and four vertical side members, two opposite ones of said vertical side members including handle means for enabling the user to carry side enclosure base, each of two opposite ones of said vertical side members having a pair of upwardly projecting positioning studs;
   a U-shaped instrument rack adapted for being removably positioned on said horizontal floor member of said enclosure base, said U-shaped instrument rack having a horizontal floor member, including feet means for elevating said floor member of said U-shaped instrument rack above said floor member of said enclosure base when said U-shaped instrument rack is positioned on said floor member of said enclosure base, said U-shaped instrument rack having two opposite vertical side members, including handle means for enabling the user to grasp said U-shaped instrument rack, each of said opposite vertical side members of said U-shaped instrument rack having a plurality of correspondingly shaped and positioned vertical slots opening at a top edge of each of said opposite vertical side members for retaining a plurality of surgical instruments such that a shaft portion of each of said plurality of surgical instruments is supported within a pair of corresponding slots of said opposite vertical side members of said U-shaped instrument rack, thereby permitting a handle portion of each of said plurality of surgical instruments to freely depend from said shaft portion;

an operative assembly tray, said operative assembly tray including fastener means positioned for removable engagement with said upwardly projecting positioning studs of said enclosure base for removably attaching said operative assembly tray atop said enclosure base, said operative assembly tray including a plurality of apertures and upwardly projecting guide members for receiving disassembled parts of a plurality of surgical instruments, a corresponding location on said operative assembly tray at which each of the disassembled parts of said plurality of surgical instruments is received being identified by an outline of each of said disassembled parts, and said operative assembly tray including four upwardly projecting positioning studs generally aligned with said positioning studs of said enclosure base; and a cover for covering said enclosure base, said U-shaped instrument rack positioned within the enclosure base, and said operative assembly tray positioned atop the enclosure base, said cover including fastener means positioned for removable engagement with said upwardly projecting positioning studs of said operative assembly tray for removably attaching said cover atop said operative assembly tray, said cover including a plurality of downwardly projecting flexible strips for exerting pressure on the disassembled parts of said plurality of surgical instruments received on said operative assembly tray to thereby retain them in their corresponding locations on said operative assembly tray.

2. A surgical tray system as in claim 1 wherein said enclosure base, said U-shaped instrument rack, said operative assembly tray, and said cover each include a multiplicity of vent slots to promote movement of air during sterilization of the plurality of surgical instruments retained by said U-shaped instrument rack and the disassembled parts of said plurality of surgical instruments retained on said operative assembly tray when said surgical tray system is positioned in an autoclave.

3. A surgical tray system as in claim 1 further comprising one or more additional assembly trays, each of which is constructed like said operative assembly tray, each of which is adapted for receiving disassembled parts of an additional plurality of surgical instruments, and each of which is sequentially stacked on top of said operative assembly tray.

4. A surgical tray system as in claim 1 wherein:
said handle means of said enclosure base comprises a pair of outwardly directed flanges;
said handle means of said U-shaped instrument rack comprises a pair of outwardly directed flanges;
said operative assembly tray includes a pair of outwardly directed flanges that serve as handles; and
said cover includes a pair of outwardly directed flanges that serve as handles.

5. A surgical tray system as in claim 1 wherein said enclosure base, said U-shaped instrument rack, said operative assembly tray, and said cover are fabricated on anodized aluminum.

6. A surgical tray system as in claim 1 wherein said floor member of said enclosure base included retention means for retaining said U-shaped instrument rack in a fixed position within said enclosure base.

7. A surgical tray system as in claim 6 wherein said retention means comprises a plurality of raised members that prevent slippage of said U-shaped instrument rack on said floor member of said enclosure base.

8. A surgical tray system as in claim 1 wherein the opposite vertical side members of said U-shaped instrument rack include one or more corresponding pairs of apertures for retaining one or more shaft instruments.

9. A surgical tray system as in claim 1 wherein said outline of each of said disassembled parts of said plurality of surgical instruments received by said operative assembly tray comprises a silhouette of each instrument part silk-screened on a top surface of said operative assembly tray.

10. A surgical tray system as in claim 1 wherein the number of slots in said opposite vertical side members of said U-shaped instrument rack is equal to the number of surgical instruments required to perform a particular endoscopic surgical procedure.

11. A surgical tray system as in claim 1 wherein the disassembled parts of the plurality of surgical instruments received by said operative assembly tray are arranged in the order in which they are required during a particular surgical procedure.

* * * * *